US008115482B2

(12) United States Patent
Hughes

(10) Patent No.: US 8,115,482 B2
(45) Date of Patent: Feb. 14, 2012

(54) MAGNETIC RESONANCE ANATOMICAL IMAGE GENERATING METHOD AND SYSTEM

(75) Inventor: Timothy Hughes, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 84 days.

(21) Appl. No.: 12/125,502

(22) Filed: May 22, 2008

(65) Prior Publication Data

US 2009/0015257 A1 Jan. 15, 2009

(30) Foreign Application Priority Data

May 23, 2007 (DE) .......................... 10 2007 023 846

(51) Int. Cl.
*G01V 3/00* (2006.01)
*A61B 5/055* (2006.01)
(52) U.S. Cl. ........ 324/309; 324/307; 324/318; 324/306; 600/410
(58) Field of Classification Search .......... 324/300–322; 600/410–435; 382/128–131
See application file for complete search history.

(56) References Cited

U.S. PATENT DOCUMENTS

| | | | | |
|---|---|---|---|---|
| 4,585,992 A * | 4/1986 | Maudsley et al. | ............. | 324/309 |
| 5,204,627 A * | 4/1993 | Mistretta et al. | ............. | 324/309 |
| 5,560,360 A * | 10/1996 | Filler et al. | ................... | 600/408 |
| 6,477,398 B1 * | 11/2002 | Mills | ............................. | 600/409 |
| 7,069,068 B1 * | 6/2006 | Ostergaard | .................... | 600/420 |
| 7,642,775 B2 * | 1/2010 | Katscher et al. | ............. | 324/307 |
| 2001/0039377 A1 * | 11/2001 | Maier et al. | .................... | 600/410 |
| 2005/0256393 A1 | 11/2005 | Deoni et al. | .................. | 600/410 |
| 2008/0077006 A1 * | 3/2008 | Katscher et al. | ............. | 600/414 |
| 2008/0218506 A1 * | 9/2008 | Doyle | ........................... | 345/418 |
| 2008/0221433 A1 * | 9/2008 | Doyle | ........................... | 600/422 |
| 2009/0015257 A1 * | 1/2009 | Hughes | ......................... | 324/309 |
| 2010/0271021 A1 * | 10/2010 | Liu et al. | ........................ | 324/309 |
| 2010/0301860 A1 * | 12/2010 | Kim et al. | ...................... | 324/309 |
| 2011/0044524 A1 * | 2/2011 | Wang et al. | .................... | 382/131 |
| 2011/0199084 A1 * | 8/2011 | Hasan | ............................ | 324/309 |
| 2011/0234225 A1 * | 9/2011 | Bieri et al. | ..................... | 324/309 |

OTHER PUBLICATIONS

"T2 Quantitation of Articular Cartilage at 1.5 T," Maier et al., J. of Mag. Res. Imaging, vol. 17 (2003) pp. 356-364.

* cited by examiner

*Primary Examiner* — Melissa Koval
*Assistant Examiner* — Tiffany Fetzner
(74) *Attorney, Agent, or Firm* — Schiff Hardin LLP

(57) ABSTRACT

In a method to generate an anatomical image of an examination area with a magnetic resonance apparatus as well as computer program and magnetic resonance apparatus for implementation of the method, at least one image data set of the examination area and a parameter value map are loaded. The at least one loaded image data set and the loaded parameter value map are processed into an anatomical image. The processing includes a weighting of elements of the at least one image data set with a weighting factor. The weighting factor depends on a parameter value of the parameter value map corresponding to the respective element of the image data set. The generated weighted anatomical image is displayed and/ or stored.

18 Claims, 3 Drawing Sheets

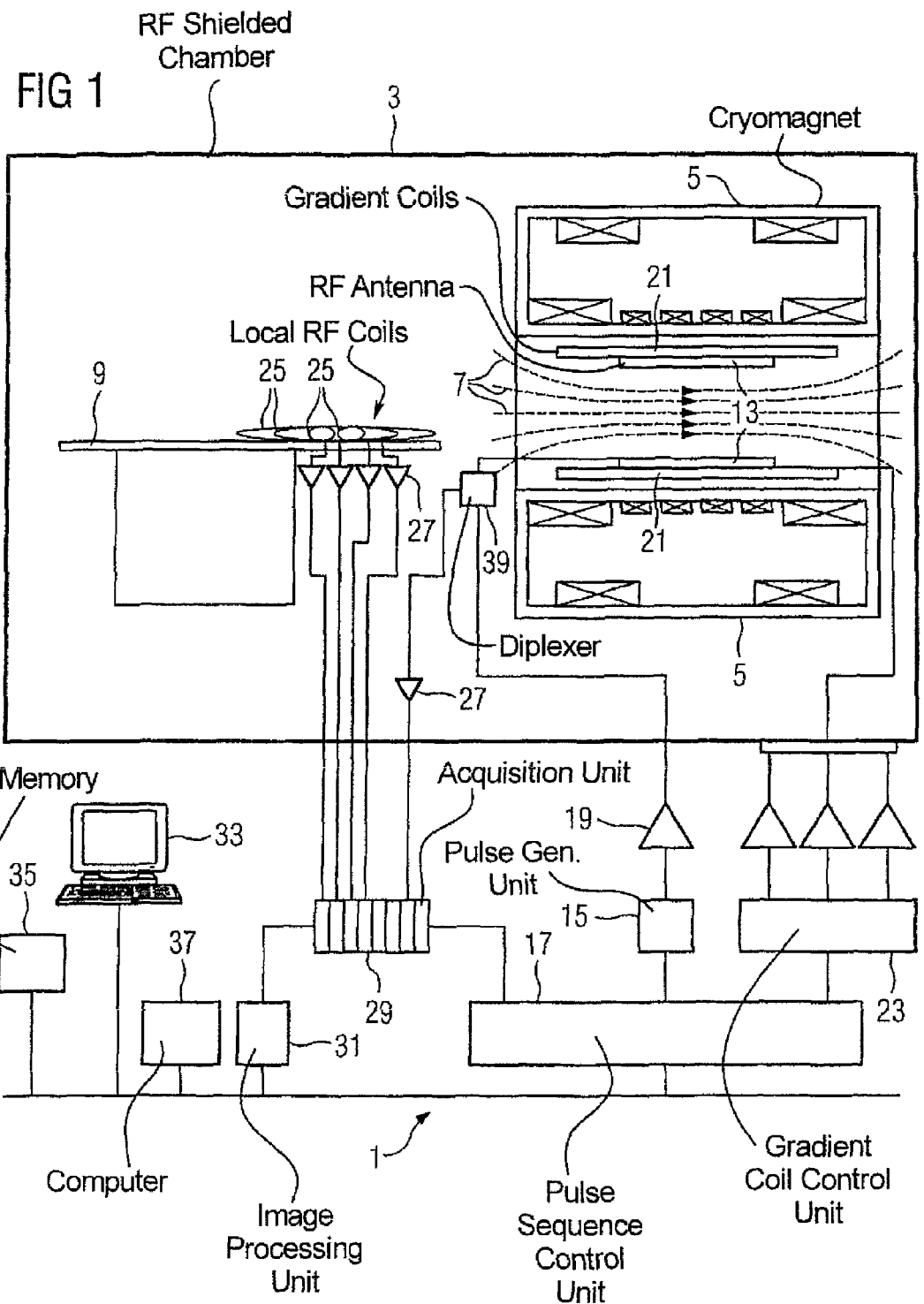

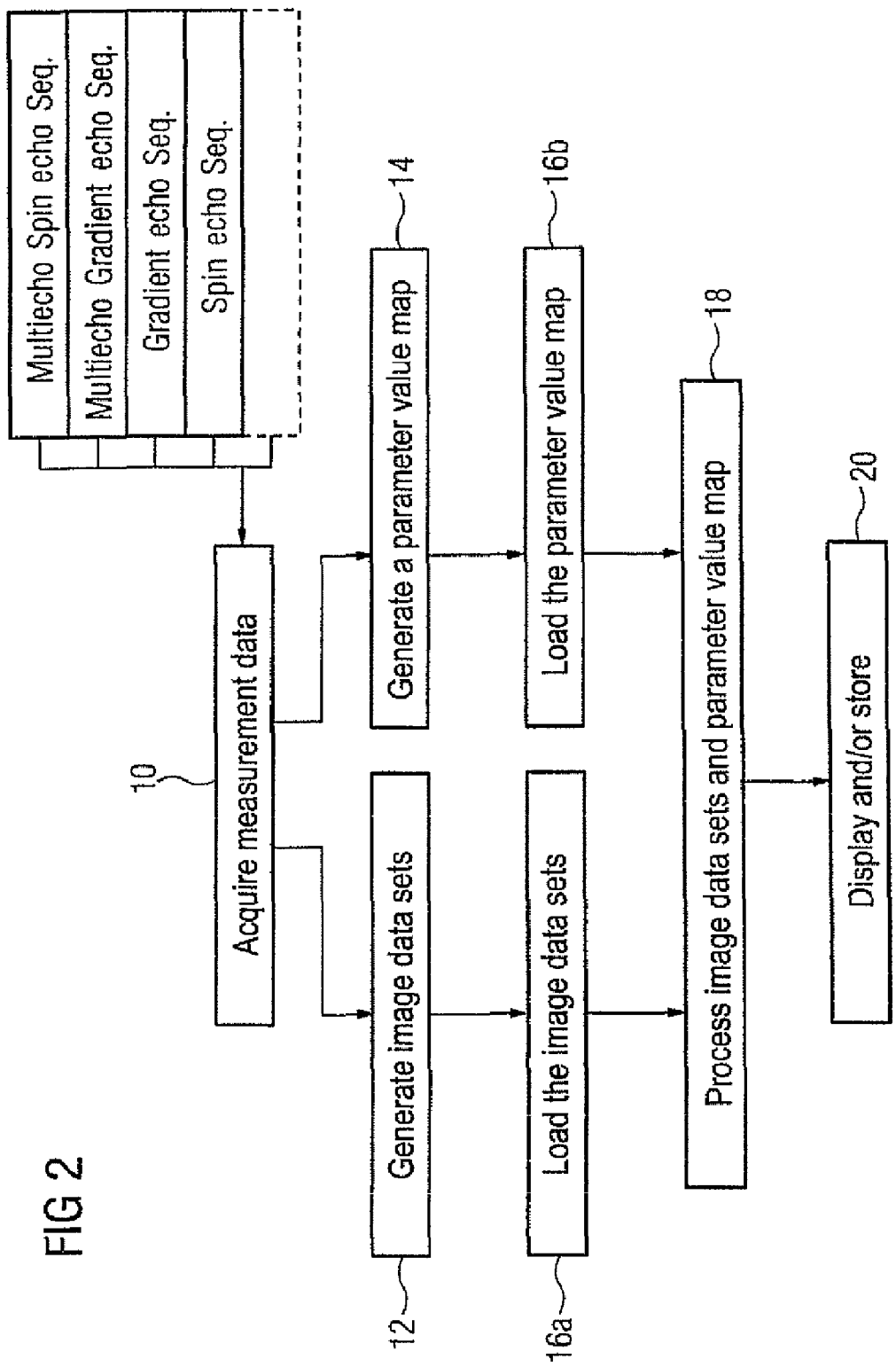

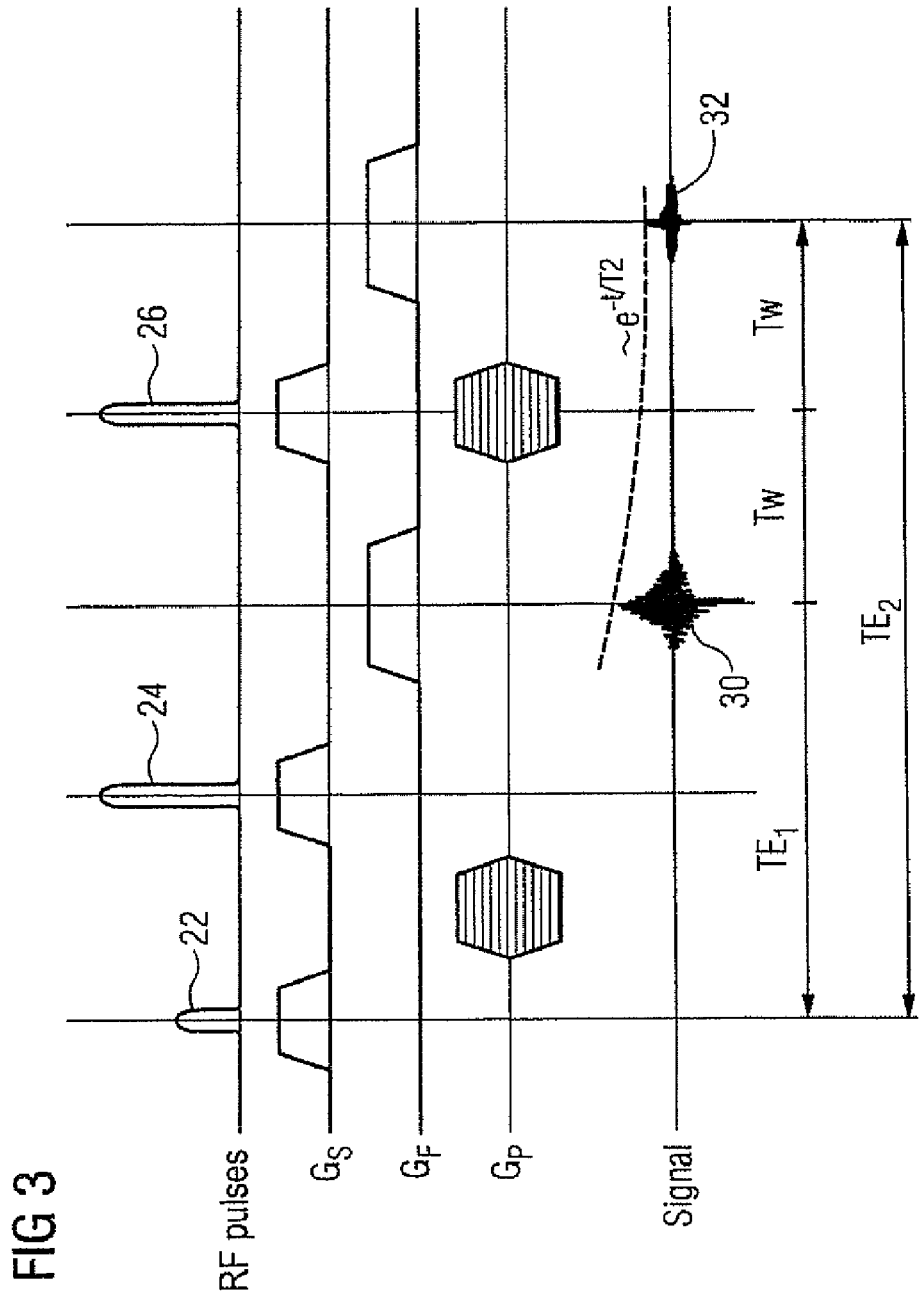

MAGNETIC RESONANCE ANATOMICAL IMAGE GENERATING METHOD AND SYSTEM

BACKGROUND OF THE INVENTION

1. Field of the Invention

The present invention concerns a method for generation of an anatomical image of an examination area with a magnetic resonance apparatus.

The invention also concerns a computer program and a magnetic resonance apparatus for implementation of the method.

2. Description of the Prior Art

Magnetic resonance (MR) is a known modality with which images of the inside of an examination subject can be generated. Expressed in a simplified way, the examination subject is positioned in a strong, static, homogeneous basic magnetic field (field strengths of 0.2 Tesla to 7 Tesla and more) in an MR such that the nuclear spins of the examination subject orient along the basic magnetic field.

To trigger nuclear magnetic resonance signals, radio-frequency excitation pulses are radiated into the examination subject, the triggered nuclear magnetic resonance signals are measured and MR images are reconstructed based thereon. The MR imaging enables image contrasts that result from the combination of multiple parameters. Important MR parameters are, for example, the density of the excited nuclear spins (primarily hydrogen protons); the relaxation times for magnetizations ($T1$, $T2$, $T2^*$) of the examined tissue; the magnetization transfer; and diverse additional contrast mechanisms.

For spatial coding of the measurement data, rapidly switched gradient fields are superimposed on the basic magnetic field. The acquired measurement data are digitized and stored in a k-space matrix as complex number values. An associated MR image can be reconstructed from the k-space matrix populated with values by means of a multi-dimensional Fourier transformation.

Depending on the type of the examination and of the examination subject, an acquisition sequence is selected that exhibits those MR parameters that generate an advantageous image contrast for the examination. Value maps in which the distribution of only a single MR parameter is listed make the diagnosis easier for specific examinations.

For example, in the functional imaging of cartilage tissue value maps of the relaxation times $T2$ and $T2^*$ have been used for some time in order to monitor the course of a therapy or an illness (such as, for example, osteoarthritis). For this purpose, multi-echo gradient echo sequences or multi-echo spin echo sequences are used for generation of $T2^*$ maps or $T2$ maps, wherein the measured data of the respective multi-echo sequences are fitted to the respective relaxation equations in order to obtain a value map of the corresponding relaxation parameter.

Maier et al. describe such a procedure in "T2 Quantitation of Articular Cartilage at 1.5 T", Journal of Magnetic Resonance Imaging 17: 358-364 (2003) using a $T2$ value map in connection with examinations of patellae.

Further application fields of such parameter value maps to support a diagnosis are, for example, the field of liver examinations, in particular for examination and monitoring of an iron uptake of the liver (hemachromatosis) or examination of the nerve bundle at a spinal column.

$T2^*$ and $T2$ value maps can also be generated in a known manner without multi-echo sequences when a number of individual measurements of an examination area are implemented in order with the same repetition time but different echo times. The generation of $T1$ value maps is likewise known, for example from a series of measurements (at least two) with different repetition times TR but the same echo time. Further measurement sequences are known that are used for a generation of MR parameter value maps, also with regard to other MR parameters.

In order to increase the usage of these parameter value maps and in particular to enable a precise localization of the conditions presented in the parameter value map, however, the parameter value maps should be associated with a corresponding anatomical image. However, this procedure requires a high degree of qualification and training since the parameter value maps must be manually adapted to an associated anatomical image.

Moreover, specific image information of the anatomical image can interfere with the desired information about, for example, the cartilage tissue in the combined image. For example, osseous tissue that is not important for the monitoring of cartilage tissue but possibly exhibits similar contrasts can optically deflect.

SUMMARY OF THE INVENTION

An object of the present invention is to enable the generation of an image in which both the anatomy and the distribution of relevant MR parameters are recognizable.

The above object is achieved according to the invention by a method and MR system for generation of an anatomical image of an examination area wherein at least one image data set of the examination area and a parameter value map are loaded into a processor. The at least one loaded image data set as well as the loaded parameter value map are processed into an anatomical image. The processing includes a weighting of elements of the at least one image data set with a weighting factor. The weighting factor depends on a parameter value of the parameter value map corresponding to the respective element of the image data set. The generated weighted anatomical image is displayed and/or stored.

This enables in a simple manner a fast and effective visualization of fluctuations of an MR parameter in the anatomy of the examination area.

The at least one loaded image data set was advantageously used for the generation of the parameter value map. In a simple manner it is thus ensured that image data set and value map reproduce the exact same examination area.

In an embodiment of the invention the parameter value map was generated from at least two image data sets of the examination area, with only echo signals of a specific echo time of measurement data of the examination area being used for a generation of every single image data set, and with the echo times of the echo signals that differ for different image data sets. The use of multiple image data sets in the generation of the parameter value map also allows the use of multiple (at least two) image data sets in the processing into an anatomical image, which offers advantages by averaging.

In a further embodiment, the examination area encompasses cartilage. Parameter value maps are directly suitable for a diagnosis of cartilage tissue.

In another embodiment the parameter is a time constant of the transversal magnetic relaxation ($T2$) or a time constant of the true decay of the transversal magnetization ($T2^*$) or a time constant of the longitudinal magnetic relaxation ($T1$). Particularly simple value maps can be created for the time constants of the magnetic resonance technique. The diagnostic use is simultaneously very high.

The above object also is achieved in accordance with the present invention by a computer-readable medium encoded with programming instructions that cause a processor, loaded with the aforementioned image data set of the examination area and the aforementioned parameter value map, to implement the processing described above in connection with the inventive method and system.

BRIEF DESCRIPTION OF THE DRAWINGS

FIG. 1 schematically illustrates a magnetic resonance apparatus.

FIG. 2 is a flowchart of an exemplary embodiment of a method for generation of an anatomical image of an examination area with a magnetic resonance apparatus in accordance with the invention.

FIG. 3 shows an example of a measurement sequence suitable for the inventive method.

DESCRIPTION OF THE PREFERRED EMBODIMENTS

FIG. 1 schematically shows the basic components of a magnetic resonance apparatus 1. In order to examine a body by means of magnetic resonance imaging, various magnetic fields matched to one another as precisely as possible in terms of their temporal and spatial characteristics are radiated at the body.

A strong magnet (typically a cryomagnet 5 with a tunnel-shaped opening) arranged in a radio-frequency-shielded measurement chamber 3 generates a static, strong basic magnetic field 7 that is typically 0.2 Tesla to 7 Tesla and more. A body or a body part to be examined (not shown here) is borne on a patient bed 9 and positioned in a homogeneous region of the basic magnetic field 7.

The excitation of the nuclear spins of the body ensues via magnetic radio-frequency excitation pulses that are radiated via a radio-frequency antenna (shown here as a body coil 13). The radio-frequency excitation pulses are generated by a pulse generation unit 15 that is controlled by a pulse control unit 17. After an amplification by a radio-frequency antenna 19 they are conducted to the radio-frequency antenna. The radio-frequency system shown here is merely schematically indicated. More than one pulse generation unit 15, more than one radio-frequency amplifier 19 and multiple radio-frequency antennas are typically used in a magnetic resonance apparatus 1.

Furthermore, the magnetic resonance apparatus 1 has gradient coils 21 with which magnetic gradient fields for selective slice excitation and for spatial coding of the measurement signal are radiated in a measurement. The gradient coils 21 are controlled by a gradient coil control unit 23 that, like the pulse generation unit 15, is connected with the pulse sequence control unit 17.

The signals emitted by the excited nuclear spins are received by the body coil 13 and/or by local coils 25, amplified by associated radio-frequency preamplifiers 27 and processed further and digitized by an acquisition unit 29.

Given a coil that can be operated both in transmission mode and in acquisition mode (such as the body coil 13, for example), the correct signal relaying is regulated by an upstream transmission-reception diplexer 39.

An image processing unit 31 generates from the measurement data an image that is presented to a user via a control console 33 or is stored in a memory storage unit 35.

A central computer 37 controls the individual system components, for example during the acquisition of the measurement data. The computer 37 is fashioned such that the inventive method can be implemented with the computer 37 together with the pulse sequence controller unit 17 controlled by the computer 37 and with the image processing unit 31. For example, for this purpose an inventive computer program can be executed on the computer 37 and possibly also installed on the image processing unit 31.

The computer 37 can also be formed of multiple sub-units, of which at least one can also be operated independently of a magnetic resonance apparatus 1.

FIG. 2 shows a workflow diagram of an exemplary method for generation of an anatomical image of an examination area with a magnetic resonance apparatus.

Measurement data of at least one measurement sequence with which the desired MR parameters can be shown are thereby acquired in a first step 10. A series of suitable sequences are listed at the top right in FIG. 2, for example (multi-echo) gradient echo sequences for the T2* parameter or (multi-echo) spin echo sequences for the T2 parameter. The multi-echo sequences generate at least two echo signals at echo times $TE_i$ (i∈N) after an excitation pulse. It thereby applies that: $TE_i \neq TE_j$ if i≠j (j∈N). The acquired measurement data of each echo signal are digitized in a known manner and stored in a k-space matrix as complex number values, wherein a separate k-space matrix exists for each echo time $TE_i$.

In a further step 12 an image data set $I_i(x,y)$ is generated by means of known transformation techniques from at least one of the k-space matrices populated with values. $I_i(x,y)$ is hereby the intensity in the image element with the coordinates (x,y) of the image data set belonging to the echo time $TE_i$.

In a further step 14, a spatially resolved parameter value map (for example a value map of the relaxation constant T2 (x,y) of the transversal magnetization or of the time constant of the free induction decay T2*(x,y) or a value map of a further MR parameter) is generated from the acquired measurement data. For example, this occurs by fitting the measurement data of the various echo signals to corresponding relaxation equations.

The at least one image data set $I_i(x,y)$ and the generated parameter value map are loaded in the steps 16a and 16b. As already noted, there are also other possibilities in order to arrive at the at least one image data set and the parameter value map for the inventive method. The steps 10 through 14 merely provide an example.

The at least one image data set $I_i(x,y)$ is processed into a relaxation-weighted anatomical image in a processing step 18. For this the at least one image data set $I_i(x,y)$ is weighted depending on the associated relaxation parameter value (for example T2(x,y)) and the associated characteristic time value (for example the echo time $TE_i$).

In an embodiment the at least one loaded image data set and the loaded parameter value map are processed according to the following formula:

$$I(x, y) = \frac{1}{N}\sqrt{\sum_{i=1}^{N}(I_i(x, y)\cdot \exp\{-T_i/T_{rel}(x, y)\})^2}.$$

I(x,y) is the intensity value of the relaxation-weighted anatomical image at the coordinate (x,y), N is the number of the different image data sets $I_i(x,y)$ used for processing, $I_i(x,y)$ is the intensity value of the i-th image data set at the coordinate (x,y), $T_i$ is the time value characteristic of the image data set $I_i(x,y)$, for example the echo time $TE_i$ (if $T_{rel}$ is T2 or T2*) or the repetition time TR (if $T_{rel}$ is T1). $T_{rel}(x,y)$ is the parameter value at the coordinate (x,y). $T_{rel}$ stands for T1, T2 or T2*. It is understood that N cannot be greater than the maximum number of the echo signals after the excitation pulse.

The at least one loaded image data set $I_i(x,y)$ is thus multiplied per element (i.e. for every possible combination of x with y) with a weighting factor that exponentially decreases with the ratio of respective echo time $TE_i$ of the image data set $I_i(x,y)$ to respective parameter value $T_{rel}(x,y)$. If more than one image data set $I_i(x,y)$ was loaded, identical elements of the different image data sets $I_i(x,y)$ are initially squared after the multiplication with the weighting factor, added, and then the square root is taken. The result is divided by the number of the loaded image data sets N.

Possibly only a portion of the elements of the at least one image data set is weighted. For example, only the element with the coordinates (x,y) with $x \in [x_{min}; x_{max}]$ and $y \in [y_{min}; y_{max}]$ where an assistance with a diagnosis is desired may be weighted.

In a simpler embodiment of the method, the squaring of the weighted intensity values of the image data sets and the subsequent taking of the square root and/or the division by the number N of the various image data sets used for processing are omitted. This procedure also leads to an acceptable result but is not entirely mathematically correct. Moreover, the average achieved with the above, mathematically correct formula can have a positive influence on the end result.

The weighted anatomical image generated in the processing step 18 is displayed and/or stored in a step 20.

FIG. 3 shows an example of a measurement sequence suitable for the method according to the invention in an example of a double echo spin echo sequence.

An excitation pulse 22 (for example a 90° pulse) excites the spins in the examination area. After half of an echo time $TE_1$, an additional pulse 24 (what is known as a rephasing or 180° pulse 24) is radiated. This pulse 24 ensures that a first echo signal 30 is generated at the time $TE_1$. After a wait time $T_w$ after the first echo signal 30, a second 180° pulse 26 is radiated that generates a second echo signal 32 after an echo time $TE_2 = TE_1 + 2*T_w$.

For spatial coding of the magnetic resonance signals, pulse-shaped magnetic gradient fields are generated in the three independent spatial directions.

An identical slice-selection gradient $G_S$ for selection of a respectively identical slice in the examination subject is respectively radiated upon the radiation of each pulse 22, 24, 26. Phase coding gradients $G_P$ are radiated between slice selection and echo signal. An identical frequency coding gradient $G_F$ is respectively radiated during the readout of the echo signals 30 and 32.

In this case the maximum amplitude of each signal falls exponentially with the ratio of the time to the time constant T2. For example, a T2 value map can thus be calculated from two image data sets that were acquired at the echo times $TE_1$ and $TE_2$ in the described manner.

The spin echo pulse sequence shown in FIG. 3 is repeated with various phase coding gradients $G_P$ (indicated by the horizontal lines in the pulses of the phase coding gradients $G_P$) until the k-space matrix is filled with sufficient values for image reconstruction.

For example, multi-echo gradient echo sequences (such as FLASH, for instance) are suitable for the calculation of a T2* value map.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an anatomical image of an examination area of a subject by magnetic resonance, comprising the steps of:
    loading at least one magnetic resonance image data set, representing a tissue-containing examination area of a subject into a processor, said image data set being comprised of image elements collectively representing a spatially resolved anatomical image of said examination area, said tissue exhibiting a magnetic resonance relaxation time constant that affects a visual appearance of said anatomical image;
    loading a spatially resolved relaxation parameter value map of said examination area of said subject into said processor, said relaxation parameter value map being comprised of map elements at respective locations in said parameter value MAP corresponding to respective locations of said image elements in said image data set, and collectively representing a spatially resolved mapping of values calculated from, and thus differing from, of said magnetic resonance relaxation time constant of said tissue at locations respectively corresponding to and matching said locations of said image elements in said anatomical image;
    in said processor, processing said at least one magnetic resonance image data set and said relaxation parameter value map to form a weighted anatomical image of the examination area, by weighting respective image elements of said anatomical image represented by said at least one magnetic resonance image data set with respective weighting factors that depend on respective values of said magnetic resonance relaxation time constant in said relaxation parameter value map at said map elements at locations respectively corresponding to the locations of the respective image elements in the magnetic resonance image data set; and
    making said weighted anatomical image available as an output from the processor in a form for at least one of display or storage thereof.

2. A method as claimed in claim 1 comprising generating said relaxation parameter value map from said at least one magnetic resonance image data set of the examination area.

3. A method as claimed in claim 1 comprising generating said relaxation parameter value map at least two magnetic resonance image data sets of the examination area that respectively comprise echo signals that are different for each magnetic resonance image data set, and wherein each magnetic resonance image data set comprises only echo signals exhibiting a predetermined echo time.

4. A method as claimed in claim 3 comprising generating said at least two magnetic resonance image data sets from measurement data obtained using a measurement sequence comprising two echo signals after each excitation pulse.

5. A method as claimed in claim 1 wherein said at least one magnetic resonance image data set comprises data representing an echo time, and comprising using, as said weighting factor, a ratio of said echo time to the respective parameter value.

6. A method as claimed in claim 5 comprising exponentially decreasing said weighting factor with said ratio.

7. A method as claimed in claim 1 wherein said at least one image data set comprises data representing an echo time and also exhibits a time value characteristic other than said echo time, and comprising using, as said weighting factor, a ratio of said time value characteristic to the respective parameter value.

8. A method as claimed in claim 7 comprising exponentially decreasing said weighting factor with said ratio.

9. A method as claimed in claim 1 wherein said magnetic resonance image data set represents intensity values and comprising processing said at least one magnetic resonance image data set and said relaxation parameter value map by performing at least one of addition of and multiplication of said intensity values.

10. A method as claimed in claim 1 comprising loading at least two magnetic resonance image data sets of said examination area into said processor and processing said at least two magnetic resonance image data sets and said relaxation parameter value map into respective at least two weighted anatomical images.

11. A method as claimed in claim 10 comprising averaging said at least two weighted anatomical images to produce said weighted anatomical image at said output of said processor.

12. A method as claimed in claim 1 comprising loading at least one image data set into the processor of an examination area that encompasses cartilage.

13. A method as claimed in claim 1 comprising employing, as said magnetic resonance relaxation time constant, a time constant selected from the group consisting of a time constant of the transverse magnetic relaxation T2 and a time constant of the true decay of the transverse magnetization T2*.

14. A method as claimed in claim 1 comprising employing, as said magnetic resonance relaxation time constant, a time constant of the longitudinal magnetic relaxation T1.

15. A method as claimed in claim 1 wherein said at least one magnetic resonance image data set comprises loading multiple magnetic resonance image data sets into said processor, each of said multiple magnetic resonance image data sets comprising data representing an echo time and being comprised of a plurality of image elements, and comprising processing each of said multiple magnetic resonance image data sets in said processor by multiplying each image element thereof with a weighting factor that decreases exponentially with a ratio of the echo time represented by that magnetic resonance image data set to the respective parameter value, and squaring corresponding elements of respective magnetic resonance image data sets after multiplication with said weighting factor and adding the squares to obtain a sum, and dividing the square of the sum by the number of said multiple magnetic resonance image data sets.

16. A method as claimed in claim 1 wherein said at least one magnetic resonance image data set comprises loading multiple magnetic resonance image data sets into said processor, each of said multiple magnetic resonance image data sets comprising data representing a time value characteristic, other than echo time, and being comprised of a plurality of image elements, and comprising processing each of said multiple magnetic resonance image data sets in said processor by multiplying each image element thereof with a weighting factor that decreases exponentially with a ratio of the time value characteristic represented by that magnetic resonance image data set to the respective parameter value, and squaring corresponding elements of respective magnetic resonance image data sets after multiplication with said weighting factor and adding the squares to obtain a sum, and dividing the square of the sum by the number of said multiple magnetic resonance image data sets.

17. A non-transitory computer-readable storage medium encoded with programming instructions, said medium being loadable into a processor of a magnetic resonance imaging system and said programming instructions causing said processor to:

receive and store therein at least one magnetic resonance image data set, representing a tissue-containing examination area of a subject, said image data set being comprised of image elements collectively representing a spatially resolved anatomical image of said examination area, said tissue exhibiting a magnetic resonance relaxation time constant that affects a visual appearance of said anatomical image;

receive and store therein a relaxation parameter value map of said examination area of said subject, said relaxation parameter value map being comprised of map elements at respective locations in said parameter value Map corresponding to respective locations of said image elements in said image data set and collectively representing a spatially resolved mapping of values calculated from, and thus differing from, said magnetic resonance relaxation time constant of said tissue at locations respectively corresponding to and matching said locations of said image elements in said anatomical image;

process said at least one magnetic resonance image data set and said relaxation parameter value map to form a weighted anatomical image, by weighting respective image elements of said anatomical image represented by said at least one magnetic resonance image data set with a weighting factor that depends on a value of said magnetic resonance relaxation time constant in the relaxation parameter value map at said map elements at locations respectively corresponding to the locations of the respective image element in the magnetic resonance image data set; and make said weighted anatomical image available at an output of the processor in a form for at least one of display or storage thereof.

18. A magnetic resonance imaging apparatus comprising:

a magnetic resonance data acquisition device that interacts with a subject in order to obtain at least one magnetic resonance image data set of a tissue-containing examination area of the subject, said image data set being comprised of image elements collectively representing a spatially resolved anatomical image of said examination area, said tissue exhibiting a magnetic resonance relaxation time constant that affects a visual appearance of said anatomical image; and a processor in communication with said data acquisition unit that is loaded with said at least one magnetic resonance image data set as well as being loaded with a relaxation parameter value map of said examination area of the subject, said relaxation parameter value map being comprised of map elements at respective locations in said parameter value Map corresponding to respective locations of said image elements in said image data set, and collectively representing a spatially resolved mapping of values calculated from, and thus differing from, said magnetic resonance relaxation time constant of said tissue at locations respectively corresponding to and matching said locations of said image elements in said anatomical image, said processor being configured in order to process said at least one magnetic resonance image data set and said relaxation parameter value map in order to form a weighted anatomical image, by weighting respective image elements of said anatomical image represented by at least one magnetic resonance image data set with a respective weighting factor that is dependent on a value of the magnetic resonance relaxation time constant in said relaxation parameter value map at said map elements at locations respectively corresponding to the locations of the respective image elements in the magnetic resonance image data set, and to make said weighted anatomical image available at an output of the processor in a form allowing at least one of display and storage thereof.

* * * * *